United States Patent
Rota et al.

(10) Patent No.: US 10,123,850 B2
(45) Date of Patent: Nov. 13, 2018

(54) INSTRUMENT FOR DRILLING DENTAL ROOT CANALS

(71) Applicant: DENTSPLY SIRONA Inc., York, PA (US)

(72) Inventors: Gilbert Rota, Vaux et Chantegrue (FR); Paul-Henri Vallotton, Pampigny (CH)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/710,869

(22) Filed: Sep. 21, 2017

(65) Prior Publication Data

US 2018/0008374 A1    Jan. 11, 2018

Related U.S. Application Data

(62) Division of application No. 14/651,677, filed as application No. PCT/IB2013/001191 on Jun. 7, 2013, now Pat. No. 9,801,696.

(30) Foreign Application Priority Data

Jan. 30, 2013   (WO) .................. PCT/IB2013/000108

(51) Int. Cl.
  *A61C 5/40* (2017.01)
  *A61C 5/42* (2017.01)
(52) U.S. Cl.
  CPC . *A61C 5/40* (2017.02); *A61C 5/42* (2017.02)
(58) Field of Classification Search
  CPC ................. A61C 3/02; A61C 5/40; A61C 5/42
  See application file for complete search history.

(56) References Cited

U.S. PATENT DOCUMENTS

| | | |
|---|---|---|
| 2,930,264 A | 3/1960 | Lovret |
| 3,400,617 A | 9/1968 | Sanborn |
| 3,824,026 A | 7/1974 | Gaskins |
| 4,044,468 A | 8/1977 | Kahn |
| 4,190,386 A | 2/1980 | Brabetz et al. |
| 4,231,692 A | 11/1980 | Brabetz et al. |
| 4,260,379 A | 4/1981 | Groves et al. |
| 4,299,571 A | 11/1981 | McSpadden |
| 4,332,561 A | 6/1982 | McSpadden |
| 4,353,698 A | 10/1982 | McSpadden |
| 4,456,411 A | 6/1984 | Clement |

(Continued)

FOREIGN PATENT DOCUMENTS

| | | |
|---|---|---|
| DE | 102006007316 A1 | 8/2007 |
| EP | 0120542 A1 | 10/1984 |

(Continued)

OTHER PUBLICATIONS

European Office Action issued in Application No. 06007527.2, dated Jun. 17, 2009.

(Continued)

*Primary Examiner* — Eric D. Bertram
(74) *Attorney, Agent, or Firm* — Dentsply Sirona Inc.

(57) ABSTRACT

An endodontic instrument comprising a tapered rod, the rod comprising an active portion, the active portion terminating at a distal tip end of the rod and defining a conical envelope, the conical envelope having a longitudinal axis that coincides with an axis of rotation of the instrument.

30 Claims, 4 Drawing Sheets

(56) References Cited

U.S. PATENT DOCUMENTS

| | | | |
|---|---|---|---|
| 4,457,710 A | 7/1984 | McSpadden | |
| 4,536,159 A | 8/1985 | Roane | |
| 4,538,989 A | 9/1985 | Apairo et al. | |
| 4,762,445 A | 8/1988 | Bunting et al. | |
| 4,842,451 A | 6/1989 | Dugger | |
| 4,850,867 A | 7/1989 | Senia et al. | |
| 4,889,487 A | 12/1989 | Lovaas | |
| 4,934,934 A | 6/1990 | Arpaio et al. | |
| 4,992,048 A | 2/1991 | Goof | |
| 5,106,298 A | 4/1992 | Heath | |
| 5,464,362 A | 11/1995 | Heath et al. | |
| 5,498,158 A | 3/1996 | Wong | |
| 5,503,554 A | 4/1996 | Schoeffel | |
| 5,584,617 A | 12/1996 | Houser | |
| 5,605,460 A | 2/1997 | Heath et al. | |
| 5,653,590 A | 8/1997 | Heath et al. | |
| 5,658,145 A | 8/1997 | Maillefer et al. | |
| 5,676,541 A | 10/1997 | Maillefer et al. | |
| 5,713,736 A | 2/1998 | Heath et al. | |
| 5,752,825 A | 5/1998 | Buchanan | |
| 5,775,904 A | 7/1998 | Riitano | |
| 5,836,764 A | 11/1998 | Buchanan | |
| 5,842,862 A | 12/1998 | Nissan | |
| 5,873,719 A | 2/1999 | Calas et al. | |
| 5,876,202 A | 3/1999 | Rouiller Jean Claude | |
| 5,882,198 A | 3/1999 | Taylor | |
| 5,897,274 A | 4/1999 | Ogura | |
| 5,897,316 A | 4/1999 | Buchanan | |
| 5,902,106 A | 5/1999 | McSpadden | |
| 5,921,775 A | 7/1999 | Buchanan | |
| 5,938,440 A | 8/1999 | McSpadden | |
| 5,975,899 A | 11/1999 | Badoz et al. | |
| 5,980,166 A | 11/1999 | Ogura | |
| 5,984,679 A | 11/1999 | Farzin-Nia | |
| 6,074,209 A | 6/2000 | Johnson | |
| 6,106,296 A | 8/2000 | Johnson | |
| 6,293,794 B1 | 9/2001 | McSpadden | |
| 6,299,445 B1 | 10/2001 | Garman | |
| 6,315,558 B1 | 11/2001 | Farzin-Nia | |
| 6,409,506 B1 | 6/2002 | Graybill | |
| 6,419,488 B1 | 7/2002 | McSpadden | |
| 6,575,748 B1 | 6/2003 | Filhol | |
| 6,702,579 B1 | 3/2004 | Hoppe et al. | |
| 6,712,611 B2 | 3/2004 | Garman | |
| 6,890,134 B1 | 5/2005 | Wagner et al. | |
| 6,929,078 B1 | 8/2005 | Randall | |
| 6,942,484 B2 | 9/2005 | Scianamblo | |
| 7,094,056 B2 | 8/2006 | Scianamblo | |
| 7,125,252 B2 | 10/2006 | Rouiller et al. | |
| 7,232,311 B1 | 6/2007 | Greggs | |
| 7,717,710 B2 | 5/2010 | Danger et al. | |
| 7,955,078 B2 | 6/2011 | Scianambio | |
| 8,454,361 B2 | 6/2013 | Scianamblo | |
| 8,496,476 B2 | 7/2013 | Scianamblo | |
| 8,727,680 B2 | 5/2014 | Wada et al. | |
| D710,009 S | 7/2014 | Maupin | |
| 8,882,504 B2 | 11/2014 | Scianamblo | |
| 8,932,056 B2 | 1/2015 | Scianamblo | |
| 9,078,722 B2 | 7/2015 | Johnson | |
| D750,246 S | 2/2016 | Scianamblo | |
| 9,271,740 B2 | 3/2016 | Scianamblo | |
| 9,277,925 B2 | 3/2016 | Scianamblo | |
| 9,351,803 B2 | 5/2016 | Scianamblo | |
| 9,662,181 B2 | 5/2017 | Scianamblo | |
| D803,399 S | 11/2017 | Scianamblo | |
| 2002/0031745 A1 | 3/2002 | Kumar et al. | |
| 2003/0068597 A1 | 4/2003 | Garman | |
| 2004/0023186 A1 | 2/2004 | McSpadden | |
| 2004/0042865 A1 | 3/2004 | Oettle | |
| 2004/0043357 A1 | 3/2004 | Ormco | |
| 2004/0131993 A1 | 7/2004 | Rouiller | |
| 2004/0185414 A1 | 9/2004 | Badoz | |
| 2004/0191723 A1 | 9/2004 | Shearer et al. | |
| 2004/0219484 A1 | 11/2004 | Scianamblo | |
| 2004/0219485 A1 | 11/2004 | Scianamblo | |
| 2004/0253379 A1 | 12/2004 | Sugita | |
| 2004/0265775 A1 | 12/2004 | Maillefer et al. | |
| 2005/0026109 A1 | 2/2005 | Buchanan | |
| 2005/0100859 A1 | 5/2005 | Graybill et al. | |
| 2005/0117984 A1 | 6/2005 | Eason | |
| 2005/0266375 A1 | 12/2005 | Brock | |
| 2005/0282109 A1 | 12/2005 | Hagermann | |
| 2005/0282117 A1 | 12/2005 | Aravena | |
| 2006/0068362 A1 | 3/2006 | Desrosiers et al. | |
| 2006/0111724 A1 | 5/2006 | Yeung | |
| 2006/0115650 A1 | 6/2006 | Hanyu et al. | |
| 2006/0216668 A1 | 9/2006 | Scianamblo | |
| 2006/0228668 A1* | 10/2006 | McSpadden | A61C 5/42 433/102 |
| 2006/0228669 A1 | 10/2006 | Scianamblo | |
| 2006/0265858 A1 | 11/2006 | McSpadden | |
| 2007/0015107 A1 | 1/2007 | Mannschedel et al. | |
| 2007/0059663 A1 | 3/2007 | Scianamblo | |
| 2007/0082318 A1 | 4/2007 | Breguet | |
| 2007/0184406 A1 | 8/2007 | Mason | |
| 2009/0047080 A1 | 2/2009 | Schweighofer et al. | |
| 2010/0221078 A1 | 9/2010 | Borschert | |
| 2011/0217673 A1 | 9/2011 | Scianamblo | |
| 2011/0236853 A1 | 9/2011 | Shimoo | |
| 2012/0034048 A1 | 2/2012 | Krieg et al. | |
| 2012/0039680 A1 | 2/2012 | Koike et al. | |
| 2012/0282571 A1 | 11/2012 | Ammon et al. | |
| 2013/0170920 A1 | 7/2013 | Ogawa | |
| 2013/0189644 A1 | 7/2013 | Johnson | |
| 2013/0273497 A1 | 10/2013 | Scianamblo | |
| 2013/0302749 A1 | 11/2013 | Scianamblo | |
| 2015/0072307 A1 | 3/2015 | Scianamblo | |
| 2015/0230902 A1 | 8/2015 | Andreou | |
| 2016/0192945 A1 | 7/2016 | Scianamblo | |
| 2017/0209236 A1 | 7/2017 | Scianamblo | |

FOREIGN PATENT DOCUMENTS

| | | |
|---|---|---|
| EP | 0987076 A2 | 3/2000 |
| EP | 1184004 A2 | 3/2002 |
| EP | 1213074 A2 | 6/2002 |
| EP | 1340573 A1 | 9/2003 |
| EP | 1361831 A1 | 11/2003 |
| FR | 2798277 A1 | 3/2001 |
| FR | 2854054 A1 | 10/2004 |
| FR | 2935260 A1 | 3/2010 |
| JP | 52-156494 A | 12/1977 |
| JP | 57-127608 A | 8/1982 |
| JP | 62-241606 A | 10/1987 |
| JP | H06-320323 A | 11/1994 |
| JP | 11-019812 A | 1/1999 |
| JP | 2002-144122 A | 5/2002 |
| JP | 2002-205213 A | 7/2002 |
| JP | 2007-0283473 | 4/2006 |
| JP | 2009502349 | 1/2009 |
| JP | 2009-108382 A | 5/2009 |
| SU | 637207 A1 | 12/1978 |
| WO | 01/19279 A1 | 3/2001 |
| WO | 02/065938 A1 | 8/2002 |
| WO | 2004/098438 A1 | 11/2004 |
| WO | 2009001681 A1 | 8/2010 |
| WO | 2012038437 | 3/2012 |
| WO | 2014/118587 A1 | 8/2014 |

OTHER PUBLICATIONS

European Office Action issued in Application No. 04750878.3, dated Jun. 5, 2007.
European Office Action issued in Application No. 04751290.0, dated Jun. 5, 2007.
International Search Report and Written Opinion issued in Application No. PCT/US2014/051916, dated Feb. 4, 2015.
International Search Report and Written Opinion issued in Application No. PCT/US2014/051909, dated Dec. 22, 2014.
European Office Action issued in Application No. 06007527.2, dated Jul. 4, 2006.
"ProTaper Next: A Shift Up in Performance,"ProTaper Next Rotary Files, Jan. 2013, 1 pages.

(56) References Cited

OTHER PUBLICATIONS

European Search Report Issued in Application No. 14838210.4, dated Mar. 8, 2017.
Japanese Office Action dated Jan. 18, 2017; Application No. 2015-554257.
Micro Mega Brochure, archive.org Jun. 26, 2011.

* cited by examiner

INSTRUMENT FOR DRILLING DENTAL ROOT CANALS

THE CROSS-REFERENCE TO RELATED APPLICATIONS

This is a Divisional application of U.S. Ser. No. 14/651,677, filed on Jun. 12, 2015, now U.S. Pat. No. 9,801,696, which is a national phase application of International Application No. PCT/IB2013/001191, filed on Jun. 7, 2013, which claims the benefit of and priority to International Application PCT/IB2013/000108, filed on Jan. 30, 2013, which are herein incorporated by reference for all purposes.

TECHNICAL FIELD

The object of the present invention is an instrument for drilling dental root canals.

BACKGROUND OF THE INVENTION

The treatment of an infected dental root is carried out by extracting the pulp using special instruments, then by shaping the root canal using successive drilling procedures, traditionally carried out with instruments of varying size and conicity. The final operation consists of filling the root canal.

The shaping of the root canal consists initially of enlarging the canal in its crown and medial parts to permit, as a second step, easier treatment of the apical part of the canal by mechanical cleaning the infected tissues.

An instrument designed for drilling dental root canals generally has a tapered rod fitted into a handle to permit it to be driven manually or mechanically and comprising, on at least part of its length, helicoidal flutes with a constant or non-constant pitch, and having at least one cutting edge.

Used in continuous rotation, this type of instrument may have a tendency to screw itself into the canal. Apart from the screwing action, another problem occurring in the production of instruments for drilling root canals is that of the strength and flexibility of the instruments. Indeed, when the instrument is too flexible it may bend or break before the practitioner has been able to complete the operation and when the instrument is too rigid, it follows the curvature of the dental root canal only with difficulty.

Numerous instruments have been developed in response to these problems. Document EP 1 361 831 describes an instrument for drilling dental canals comprising a base, a cutting section and a guiding section, the cutting section being defined by an envelope of a cylindrical or conical shape, the longitudinal axis of which coincides with the axis of rotation of the instrument. The cutting section has clearance zones disposed set-back with respect to the envelope, alternating with drilling zones disposed on said envelope.

This alternating arrangement of zones on the envelope and set back from the envelope makes it possible to reduce the risk of screwing the instrument into the dental canal. Furthermore, the axis of the cutting section can be offset with respect to the axis of the envelope. This makes it possible to deepen the clearance zones and to make the evacuation of the debris during treatment more effective.

Document U.S. Pat. No. 7,955,078 describes an endodontic instrument for preparation of dental root canals comprising a body shaped to turn about an axis of rotation. The body has a centre of mass which is not located on the axis of rotation of the instrument, thus giving the impression that the instrument is undulating ("swaggering") when it is rotated. An instrument such as this has greater flexibility and thus makes it possible to follow the complex curves of a dental root canal most effectively.

However, in these two documents the axis of the active part is offset with respect to the axis of rotation of the instrument over the whole length of said active part and in particular the axis of the point of the instrument is offset. This can generate a beating motion of the point within the canal. It thus becomes difficult to ensure optimum dimensioning of the canal during treatment, in particular in its apical portion. Moreover, a point with its axis offset also has the disadvantage of pushing the debris back towards the apical portion rather than evacuating it towards the top of the canal.

SUMMARY OF THE INVENTION

The aim of the present invention is to produce an instrument for drilling dental root canals which obviates the stated disadvantages. In particular, one aim of the present invention is thus to produce an instrument which is flexible while being strong, reliable and effective and which makes it possible at the same time to respect the initial path of the root canal to be treated and to ensure optimum dimensioning of the canal in its apical portion after treatment.

The object of the present invention is an instrument for drilling dental root canals.

BRIEF DESCRIPTION OF THE DRAWINGS

The drawings schematically illustrate by way of example a plurality of embodiments of the instrument in accordance with the invention.

DETAILED DESCRIPTION OF THE INVENTION

Figure 1:
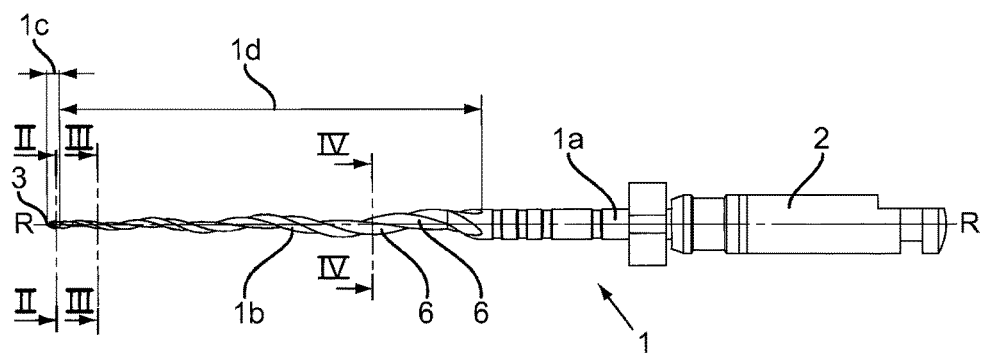
FIG. 1 illustrates a first embodiment of an instrument for drilling dental root canals in accordance with the invention.

In a first embodiment shown in FIG. 1 the instrument in accordance with the invention comprises a rod 1 fitted at one of its ends 1a in a handle 2 permitting either manual actuation of the instrument or preferably its engagement in a hand-held part providing mechanical driving of the said instrument. In particular, the instrument 1 is intended to be driven in rotation about its axis of rotation R.

The rod 1 has an active part 1b extending to the other end 3—the point 3—of the rod 1. Said active part 1b is preferably tapered and conical, narrowing to the point 3 of the rod 1. Alternatively, the active part 1b or the whole rod 1 could be cylindrical rather than conical.

The active part 1b has a polygonal cross-section (the sides of which are straight or curved) and comprises cutting edges. More particularly in this first embodiment, the active part 1b has, over its whole length, a square cross-section 4 forming four cutting edges 5a, 5b, 5c, 5d defining between them four helicoidal flutes 6, one flute being the face defined between two successive cutting edges of the active part 1b. The active part 1b is defined by an envelope 7 which is substantially tapered and has its longitudinal axis coinciding with the axis of rotation R of the instrument.

The particular feature of the instrument in accordance with the invention resides in the fact that the active part 1b has a first portion 1c extending from the point 3 towards the rear of the active part 1b and of which the centre of mass is located on the axis of rotation R of the instrument and a second portion 1d extending from the end of the first portion 1c to the rear of the active part 1b and of which at least one cross-section has a centre of mass which is not located on the axis of rotation R of the instrument but is offset with respect to said axis R. In the first embodiment shown in FIGS. 1 to 4, any cross-section of the second portion 1d of the active part 1b of the instrument 1 has a centre of mass which is not located on the axis of rotation R but is offset with respect to said axis.

Figure 2:
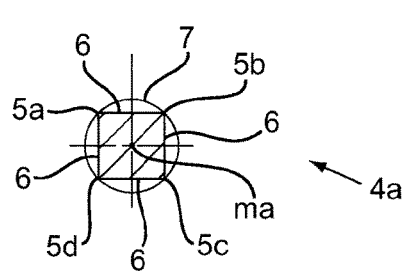
FIG. 2 is a cross-sectional view at the line II-II of the instrument shown in FIG. 1.

More precisely, and as shown in FIG. 2, in accordance with the invention any cross-section 4a of the first portion 1c has its centre of mass ma on the axis of rotation R of the instrument. Moreover, in this first embodiment the four edges 5a, 5b, 5c, 5d of such a cross-section 4a are located on the envelope 7. Thus the first portion 1c and in particular the point 3 are centred with respect to the axis of rotation R of the instrument or in other words the longitudinal axis of the first portion 1c coincides with said axis of rotation R.

Figure 3:
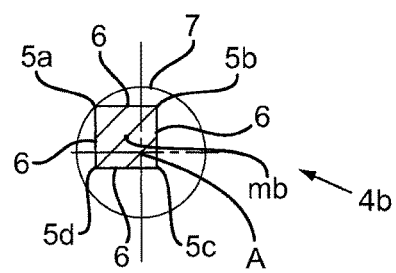
FIG. 3 is a cross-sectional view at the line III-Ill of the instrument shown in FIG. 1.
Figure 4:
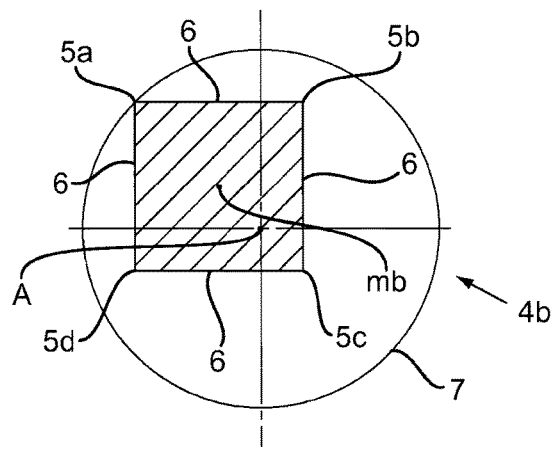
FIG. 4 is a cross-sectional view at the line IV-IV of the instrument shown in FIG. 1.

As shown in FIGS. 3 and 4, in the first embodiment, any cross-section 4b of the second portion 1d of the active part 1b has its centre of mass mb offset with respect to the axis of rotation R of the instrument and preferably a single cutting edge 5a of such a cross-section 4b is located on the envelope 7, the other cutting edges 5b, 5c and 5d being disposed inside said envelope 7. Thus in the first embodiment the whole of the second portion 1d of the active part 1b is off-centre with respect to the axis of rotation R of the instrument.

Thus an effective instrument is obtained because its point 3 is centred, does not generate any beating within the canal and has four active cutting edges.

Such an instrument in accordance with the invention can be obtained from a rod with a circular cross-section, preferably made from a nickel-titanium alloy, by providing therein helicoidal flutes by machining (milling), these flutes defining cutting edges such that the cross-section of the rod 1 is polygonal over the whole length of its active part 1b. In order to achieve the particular geometry of the active part 1b in accordance with the invention, the flutes 6 of the second portion 1d of the active part 1b are overcut with respect to the flutes 6 of the first portion 1c in order to obtain at least one cross-section 4b of said second portion 1d of which at least one cutting edge is set back within the envelope 7 and of which the centre of mass mb is offset with respect to the axis of rotation R. Thus on the second portion 1d of the active part 1b material is removed from the instrument in accordance with the invention, which makes it more flexible on this second portion than a traditional instrument which would have, over its whole active part, a cross-section with its centre of mass centred on the axis of rotation and all its edges inscribed on the envelope. By virtue of the present invention, an instrument is obtained which is effective at its point 3 while being flexible.

Preferably, in the first embodiment, the second portion 1d has a progressive offset with respect to the axis of rotation R in the direction of the rear of the instrument: i.e. a cross-section of the second portion 1d close to the point has its centre of mass less offset proportionally to the surface of the cross-section with respect to said axis of rotation R than a cross-section of the second portion 1d closer to the rear of the instrument. In terms of machining the instrument, this produces flutes 6 which are overcut proportionally more and more along the second portion 1d of the active part 1b with respect to the flutes of the first portion 1c. Thus in this first embodiment the flexibility of the instrument is adjustable and in particular increases progressively towards the rear of the active part 1b.

Preferably, the first portion 1c of the active part extends over a length of 3 millimeters starting from the point 3 of the active part 1b. In a still more preferred manner, said first portion 1c has a length of 1 millimeter.

Figure 5:
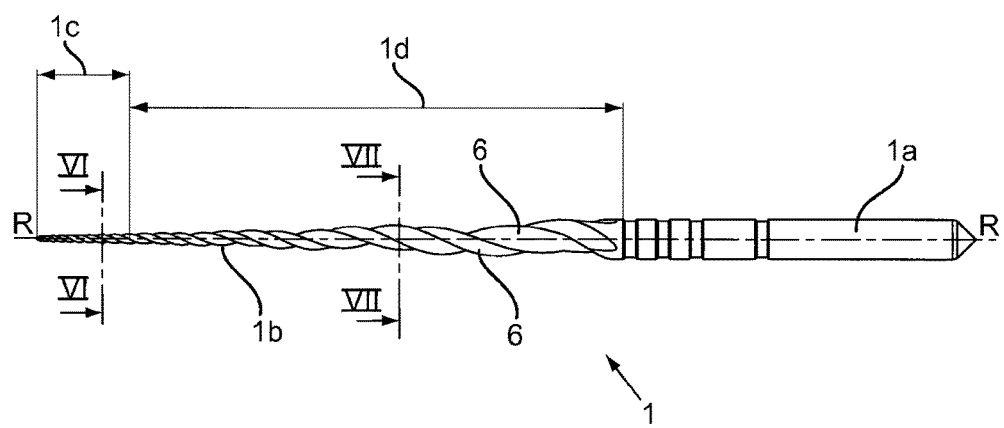
FIG. 5 illustrates a second embodiment of an instrument for drilling dental root canals in accordance with the invention.
Figure 6:
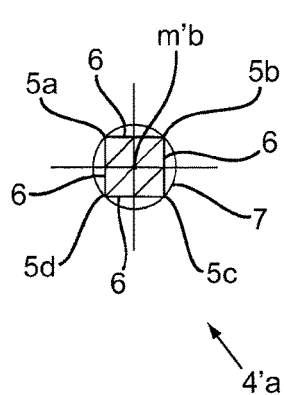
FIG. 6 is a cross-sectional view at the line VI-VI of the instrument shown in FIG. 5.
Figure 7:
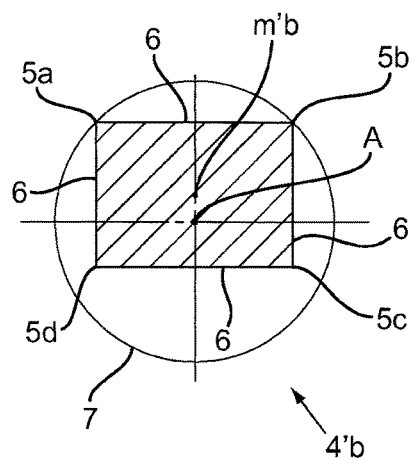
FIG. 7 is a cross-sectional view at the line VII-VII of the instrument shown in FIG. 5.
Figure 8:
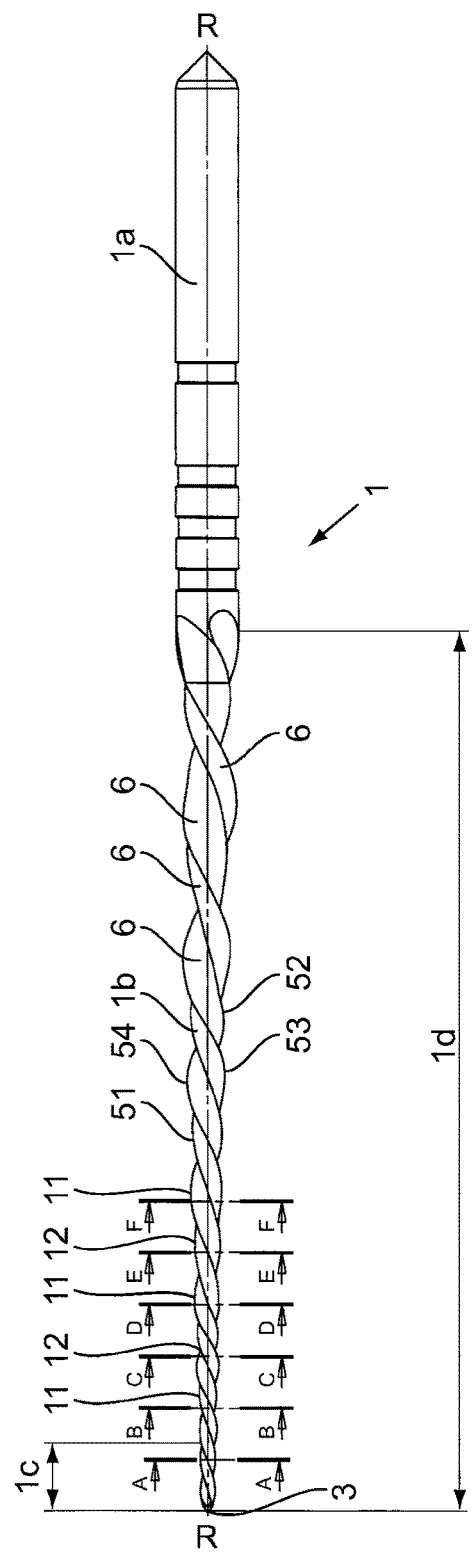
FIG. 8 illustrates a third embodiment of an instrument for drilling dental root canals in accordance with the invention.

FIGS. 5 to 7 show a second embodiment of an instrument in accordance with the invention in which the active part 1b has, over its whole length, a rectangular cross-section 4' forming four cutting edges 5a, 5b, 5c, 5d defining four helicoidal flutes 6, one flute being the face defined between two successive cutting edges of the active part 1b. As in the first embodiment, the active part 1b is defined by an envelope 7 which is substantially tapered and has the axis of rotation R of the instrument as its longitudinal axis.

The active part 1b also has a first portion 1c extending from the point 3 towards the rear of the active part 1b and having its centre of mass located on the axis of rotation R of the instrument and a second portion 1d extending from the end of the first portion 1c to the rear of the active part 1b and of which at least one cross-section has a centre of mass offset with respect to the axis of rotation R of the instrument. Preferably, and as in the first embodiment, any cross-section of the second portion 1d of the instrument in accordance with the second embodiment has a centre of mass offset with respect to the axis of rotation R.

In this second embodiment, and as shown in FIG. 6, any cross-section 4'a of the first portion 1c is square and has its centre of mass m'a on the axis of rotation R of the instrument. Furthermore, the four edges 5a, 5b, 5c, 5d of such a cross-section 4'a are located on the envelope 7 of the instrument. As shown in FIG. 7, any cross-section 4'b of the second portion 1d of the active part 1b has its centre of mass m'b offset with respect to the axis of rotation R of the instrument. In contrast to the first embodiment, for each cross-section 4'b of the second portion 1d of the active part 1c of the instrument in accordance with the second embodiment, two cutting edges 5a and 5b are on the envelope 7, the two other cutting edges 5c and 5d being disposed inside said envelope 7.

The other considerations relating to the first embodiment remain valid for this second embodiment.

As shown in FIGS. 6 and 7, the cross-sections 4'a and 4'b of the first and second portions 1c, 1d are not necessarily symmetrical, the cross-section 4'a preferably being square, while the cross-section 4'b may be rectangular.

FIGS. 8 to 14 show a third embodiment of an instrument in accordance with the invention, in which the active part 1b of the instrument has, over its whole length, a polygonal cross-section 40 of a parallelogram shape, forming four cutting edges 51, 52, 53, 54 defining four helicoidal flutes 6, one flute being the face defined between two successive cutting edges of the active part 1b. As in the previous embodiments, the active part 1b is defined by an envelope 7 which is substantially tapered and has the axis of rotation R of the instrument as its longitudinal axis.

Figure 9:
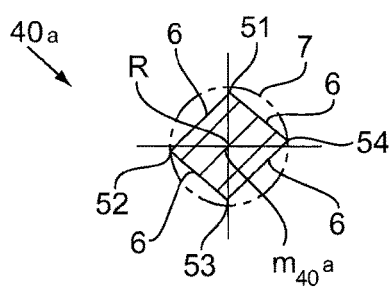
FIG. 9 is a cross-sectional view at the line A-A of the instrument shown in FIG. 8.

In accordance with the invention, the active part 1b has a first portion 1c extending from the point 3 towards the rear of the active part 1b and having its centre of mass located on the axis of rotation R of the instrument. In this third embodiment, and as shown in FIG. 9, any cross-section 40a of the first portion 1c is in the form of a parallelogram and has its centre of mass $m_{40}a$ on the axis of rotation R of the instrument. Moreover, in this embodiment, two diagonally opposed cutting edges 52, 54 of such a cross-section 40a are located on the envelope 7 of the instrument, while the other pair of diagonally opposed cutting edges 51, 53 is located set back within the envelope 7.

In accordance with the invention, the active part 1b also has a second portion 1d extending from the end of the first portion 1c to the rear of the active part 1b, of which at least one cross-section has a centre of mass which is not located on the axis of rotation R of the instrument but which is offset with respect to said axis R. In the third embodiment of the invention, and as shown in FIGS. 8 and 10 to 14, the second portion 1d has an alternating arrangement of first zones—off-centre zones 11—in which any cross-section 401b has a centre of mass $m_{401}b$ offset with respect to the axis of rotation R of the instrument and second zones—centred zones 12—in which any cross-section 402b has a centre of mass $m_{402}b$ located on the axis of rotation R of the instrument. The zone of the second portion 1d directly adjacent to the first portion 1c of the active part 1b of the instrument is an off-centre zone 11 (see FIG. 8).

Figure 10:
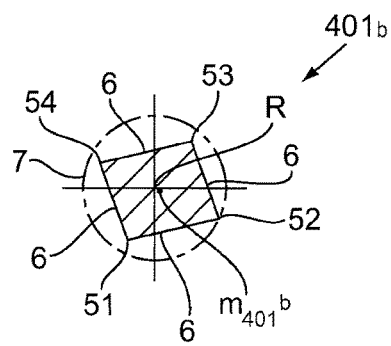
FIG. 10 is a cross-sectional view at the line B-B of the instrument shown in FIG. 8.
Figure 11:
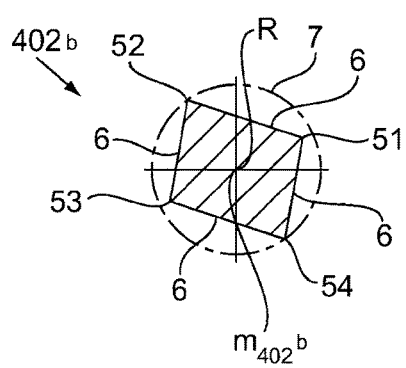
FIG. 11 is a cross-sectional view at the line C-C of the instrument shown in FIG. 8.
Figure 12:
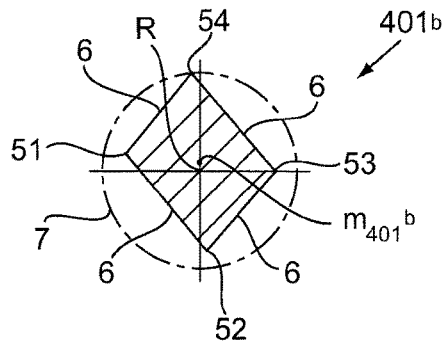
FIG. 12 is a cross-sectional view at the line D-D of the instrument shown in FIG. 8.
Figure 13:
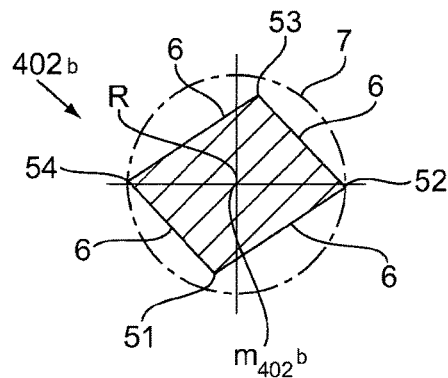
FIG. 13 is a cross-sectional view at the line E-E of the instrument shown in FIG. 8.
Figure 14:
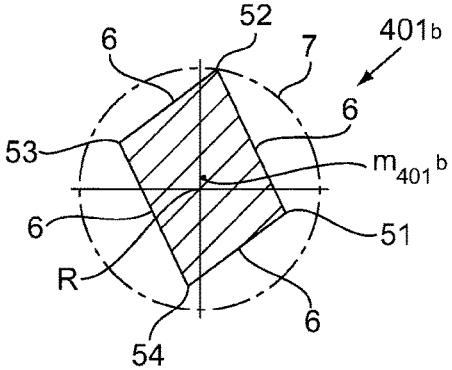
FIG. 14 is a cross-sectional view at the line F-F of the instrument shown in FIG. 8.

FIGS. 11 and 13 each show a cross-section 402b of a centred zone 12 located along the second portion 1d of the active part 1b of the instrument, while FIGS. 10, 12 and 14 each show a cross-section 401b of an off-centre zone 11 located along said second portion 1d.

Preferably, and as shown in FIGS. 11 and 13, for each cross-section 402b of a centred zone 12, two diagonally opposed cutting edges 52, 54 are located on the envelope 7 of the instrument, while the other pair of diagonally opposed cutting edges 51, 53 is located set back within the envelope 7.

In a similar, preferred manner, and as shown in FIGS. 10, 12 and 14, for each cross-section 401b of an off-centre zone 11, a single cutting edge 52, 54 appertaining to the pair of diagonally opposed cutting edges 52, 54 located on the envelope along the first portion 1c of the active part 1b of the instrument is located on the envelope 7 of the instrument, while the other cutting edges are located set back within the envelope 7.

Thus, apart from the alternation between the centred and off-centre zones 12, 11 on the second portion 1d of the active part 1b of the instrument, in this third embodiment, said second portion 1d also has an alternating arrangement between the cutting edges located on the envelope. The succession of the different zones on the second section 1d of the instrument in accordance with the third embodiment can be described as follows:

The first zone of the second portion 1d immediately adjacent to the first portion 1c of the active part 1b of the instrument is an off-centre zone 11. For each cross-section 401 b of this off-centre zone 11, only one of the two diagonally opposed cutting edges 52, 54 located on the envelope 7 for any cross-section 40a of the first portion 1c—the first cutting edge 52—is located on the envelope 7 of the instrument, the second of these cutting edges 54 and the second pair of diagonally opposed cutting edges 51, 53 being set back within the envelope 7 (FIG. 10);

The second zone is a centred zone 12. For each cross-section 402b of this centred zone 12, the first and second diagonally opposed cutting edges 52, 54 are again on the envelope 7 of the instrument, the second pair of diagonally opposed edges 51, 53 still being set back within the envelope 7 (FIG. 11);

The third zone is again an off-centre zone 11. However, in this zone the second cutting edge 54 diagonally opposed to the first 52 and which was set back within the envelope on the first zone is now located on the envelope 7, while the first cutting edge 52 is then located within the envelope 7, the second pair of diagonally opposed cutting edges 51, 53 still being set back within the envelope 7 (FIG. 12).

The following zone shown in FIG. 13 is similar to the first zone and the alternating arrangement thus extends along the second portion 1d of the active part 1b of the instrument.

Thus the instrument in accordance with the third embodiment has two cutting edges 52, 54 which are located on the envelope for any cross-section 40a of the first portion 1c of the active part 1b and for any cross-section 402b of the centred zones 12 of the second portion 1d of the active part 1b but of which at least one of the two is set back within the envelope 7 for any cross-section 401b of an off-centre zone 11 of the second portion 1d, two off-centre zones 11 separated by a centred zone 12 not having the same cutting edge on the envelope 7.

In variations, the second pair of diagonally opposed cutting edges 51, 53 could be located on the envelope 7 of the instrument for any cross-section of the active part 1b or for any cross-section of the first portion 1c or for any centred cross-section 12 of the second portion 1d. The second pair of diagonally opposed cutting edges 51, 53 could also follow the same alternating arrangement described above as the first pair of cutting edges 52, 54 along the second portion 1d of the active part 1b of the instrument.

The other considerations relating to the first two embodiments remain valid for this third embodiment.

In particular, the first portion 1c of the active part preferably extends over a length of 3 millimeters from the point 3 of the active part 1b. In a still more preferred manner, said first portion 1c has a length of 1 millimeter.

Thus as in the first two embodiments described above, the instrument in accordance with the third embodiment is effective since it has a point 3 which is centred and does not generate beating in the canal and permits precise shaping of said canal. Said instrument is also flexible at the rear owing to the presence of the off-centre zones on the second portion 1d of its active part 1b. However, in contrast to the first two embodiments in which the whole of the second portion 1d is off-centre and thus may generate a beating motion at the rear of the instrument, the alternating arrangement of centred and off-centre zones as described in the third embodiment makes it possible to ensure that the instrument is flexible while avoiding beating by ensuring the shape of the envelope generated by the instrument in rotation. Thus the instrument in accordance with the third embodiment retains all the advantages described in relation to the first two embodiments while reducing the beating motion at the rear of the instrument, a motion which could reduce the precision and speed of treatment of the dental root canal.

The embodiments presented above describe polygonal cross-sections with straight sides. It is clear that said sides could be curved. Consequently, the term "polygonal" should be understood in its general sense meaning "which has a plurality of sides" and covering equally a geometric shape with straight or curved sides.

The instrument in accordance with the invention could obviously have other known features such as variable conicity. Similarly, the flutes can be oriented equally to the right or left or even have a variable pitch.

In a general manner, the active part of an instrument in accordance with the invention has, over is whole length, a polygonal cross-section forming at least two cutting edges. The active part is defined by an essentially conical or cylindrical envelope, the longitudinal axis of which coincides with the axis of rotation of the instrument. The active part comprises a first portion extending from the point of the instrument and which is such that any cross-section of this first portion has its centre of mass on the axis of the envelope and defines at least two cutting edges which are all located on said envelope. The active part also comprises a second portion extending following the first portion towards the rear of the active part and which is such that at least one cross-section of this second portion has a centre of mass which is not located on the axis of the envelope but which is offset with respect to this axis and defines cutting edges, of which at least one is located on the envelope and at least one is located set back within said envelope.

The instrument in accordance with the invention thus has a point which is centred with respect to the axis of rotation of the instrument and a rear part, of which at least one cross-section is off-centre. The centred point makes it possible to follow the initial path of the root canal, to avoid any beating motion within said canal in the vicinity of the point and to ensure dimensioning in the preparation of the apical part of the canal. Moreover, the centred point avoids debris descending towards said apical part of the canal and contributes to successful evacuation thereof. This evacuation is further facilitated by the fact that at least one cross-section of the rear part is off-centre: the debris in fact has more space to be carried out of the canal and the off-centering of at least one cross-section of the rear part of the instrument creates a dynamic effect which lifts the debris out of the canal.

Moreover, an instrument in accordance with the present invention makes it possible to ensure strength in the part close to the point in order thus to reduce the risk of breaking the instrument in its most fragile portion. The flexibility of the instrument is not thereby reduced, since the second portion having at least one off-centre cross-section of the instrument makes the instrument flexible and this flexibility can even be progressive towards the rear of the instrument either by adjusting the off-centering of the second portion of the active part of the instrument as described in the case of the first and second embodiments or by alternating centred cross-section with off-centre cross-section along the second portion of the active part of the instrument as described in the third embodiment. Thus the instrument can be rendered sufficiently flexible to follow the complex contour of a dental root canal.

Finally, the active cutting edges of the point of the instrument, i.e. those which are located on the envelope, ensure a good level of efficacy of the instrument. At the rear, the contact zones of the instrument are reduced since some of the edges are located set back within the envelope of the instrument, which makes it possible to reduce the screwing effect and superfluous forces on the rear part of the instrument.

Thus a high-performance instrument is produced having a good balance between efficacy, flexibility and resistance to breaking and to the screwing effect.

The invention claimed is:

1. An endodontic instrument comprising:
    a tapered rod, the rod comprising an active portion, the active portion terminating at a distal tip end of the rod and defining a conical envelope, the conical envelope having a longitudinal axis that coincides with an axis of rotation of the instrument;
    the active portion comprising a plurality of helical flutes disposed along at least a segment of the active portion, the plurality of helical flutes comprising a first flute, a second flute, a third flute, and a fourth flute;
    the active portion comprising a plurality of edges, the plurality of edges comprising a first edge intersecting the first flute and the second flute, a second edge intersecting the second flute and the third flute, a third edge intersecting the third flute and the fourth flute, and a fourth edge intersecting the first flute and the fourth flute;
    the active portion comprising a first portion having a length and a second portion having a length, the second portion being disposed further from the tip end relative to the first portion;
    the first portion comprising a plurality of first portion cross-sections, the plurality of first portion cross-sections comprising a first cross-section, wherein a center of mass of the first cross-section is located on the axis of rotation of the instrument, each of the first edge, the second edge, the third edge, and the fourth edge intersecting the first cross-section, the intersection between the first edge and the first cross-section being located on the envelope;
    the second portion comprising a plurality of second portion cross-sections, the plurality of second portion cross-sections comprising a second cross-section, wherein a center of mass of the second cross-section is offset relative to the axis of rotation of the instrument, each of the first edge, the second edge, the third edge, and the fourth edge intersecting the second cross-section, the fourth flute being overcut along at least a segment of the second portion such that the third edge and the fourth edge are set back within the envelope along the segment.

2. The endodontic instrument of claim 1, wherein: the length of the second portion extends from the first portion to a proximal end of the active portion, and the fourth flute is overcut along the length of the second portion.

3. The endodontic instrument of claim 2, wherein the plurality of second portion cross-sections further comprises a third cross-section, the third cross-section having a center of mass and being disposed further from the tip end relative to the second cross-section, the distance between the center of mass of the second cross-section and the axis of rotation, considered in proportion to the size of the second cross-section, is less than the distance between the center of mass of the third cross-section and the axis of rotation, considered in proportion to the size of the third cross-section.

4. The endodontic instrument of claim 3, wherein the fourth flute is overcut proportionally more, considered relative to the rod's cross-sectional size, over the length of the second portion in a direction defined from the distal tip end toward a proximal end of the active portion.

5. The endodontic instrument of claim 2, wherein exactly two of the intersections between the second cross-section and the first, second, third, and fourth edges are located on the envelope.

6. The endodontic instrument of claim 1, wherein the plurality of second portion cross-sections further comprises a third cross-section, the third cross-section having a center of mass and being disposed further from the tip end relative to the second cross-section, the distance between the center of mass of the second cross-section and the axis of rotation, considered in proportion to the size of the second cross-section, is less than the distance between the center of mass of the third cross-section and the axis of rotation, considered in proportion to the size of the third cross-section.

7. The endodontic instrument of claim 6, wherein the fourth flute is overcut proportionally more, considered relative to the rod's cross-sectional size, over the length of the second portion in a direction defined from the distal tip end toward a proximal end of the active portion.

8. The endodontic instrument of claim 6, wherein the second cross-section is located at a distal end of the second portion, and the center of mass of the second cross-section is closer, considered in proportion to the size of the respective cross-section, to the axis of rotation than are the centers of mass of every other cross-section along the length of the second portion.

9. The endodontic instrument of claim 6, wherein a flexibility of the instrument increases in a direction defined from the tip end toward a proximal end of the active portion.

10. The endodontic instrument of claim 6, wherein exactly two of the intersections between the second cross-section and the first, second, third, and fourth edges are located on the envelope.

11. The endodontic instrument of claim 1, wherein the intersection between the second edge and the first cross-section is located on the envelope, the intersection between the third edge and the first cross-section is located on the envelope, and the intersection between the fourth edge and the first cross-section is located on the envelope.

12. The endodontic instrument of claim 11, wherein the first cross-section approximates a square, and the second cross-section approximates a rectangle.

13. The endodontic instrument of claim 11, wherein a flexibility of the instrument increases in a direction defined from the tip end toward a proximal end of the active portion.

14. The endodontic instrument of claim 1, wherein every cross-section of the first portion has a center of mass located on the axis of rotation of the instrument, and the length of the first portion is between 1 and 3 millimeters.

15. The endodontic instrument of claim 14, wherein the length of the second portion extends from the first portion to a proximal end of the active portion, and the fourth flute is overcut along the length of the second portion.

16. The endodontic instrument of claim 15, wherein every cross-section along the length of the second portion has a center of mass that is offset relative to the axis of rotation.

17. The endodontic instrument of claim 15, wherein the plurality of second portion cross-sections further comprises a third cross-section, the third cross-section having a center of mass and being disposed further from the tip end relative to the second cross-section, the distance between the center of mass of the second cross-section and the axis of rotation, considered in proportion to the size of the second cross-section, is less than the distance between the center of mass of the third cross-section and the axis of rotation, considered in proportion to the size of the third cross-section.

18. The endodontic instrument of claim 15, wherein the fourth flute is overcut proportionally more, considered relative to the rod's cross-sectional size, over the length of the second portion in a direction defined from the tip end toward the proximal end of the active portion.

19. The endodontic instrument of claim 14, wherein the plurality of second portion cross-sections further comprises a third cross-section, the third cross-section having a center of mass and being disposed further from the tip end relative to the second cross-section, the distance between the center of mass of the second cross-section and the axis of rotation, considered in proportion to the size of the second cross-section, is less than the distance between the center of mass of the third cross-section and the axis of rotation, considered in proportion to the size of the third cross-section.

20. The endodontic instrument of claim 19, wherein the second cross-section is located at a distal end of the second portion, and the center of mass of the second cross-section is closer, considered in proportion to the size of the respective cross-section, to the axis of rotation than are the centers of mass of every other cross-section along the length of the second portion.

21. The endodontic instrument of claim 1, wherein a flexibility of the instrument increases in a direction defined from the tip end toward a proximal end of the active portion.

22. The endodontic instrument of claim 1, wherein exactly two of the intersections between the second cross-section and the first, second, third, and fourth edges are located on the envelope.

23. The endodontic instrument of claim 1, wherein the length of the first portion is between 1 and 3 millimeters, the second cross-section approximates a rectangle, and every cross-section of the first portion approximates a square.

24. The endodontic instrument of claim 1, wherein at least two of the intersections between the first cross-section and first, second, third, and fourth edges are located on the envelope; and
    the length of the second portion extends from the first portion to a proximal end of the active portion, and the fourth flute is overcut along the length of the second portion.

25. The endodontic instrument of claim 24, wherein exactly two of the intersections between the second cross-section and the first, second, third, and fourth edges are located on the envelope.

26. The endodontic instrument of claim 25, wherein the plurality of second portion cross-sections further comprises a third cross-section, the third cross-section having a center of mass and being disposed further from the tip end relative to the second cross-section, the distance between the center of mass of the second cross-section and the axis of rotation, considered in proportion to the size of the second cross-section, is less than the distance between the center of mass of the third cross-section and the axis of rotation, considered in proportion to the size of the third cross-section.

27. The endodontic instrument of claim 26, wherein the intersection between the second edge and the first cross-section is located on the envelope, the intersection between the third edge and the first cross-section is located on the envelope, and the intersection between the fourth edge and the first cross-section is located on the envelope.

28. The endodontic instrument of claim 26, wherein the first cross-section approximates a square, and the second cross-section approximates a rectangle.

29. The endodontic instrument of claim 26, wherein every cross-section of the first portion has a center of mass located on the axis of rotation of the instrument, and the length of the first portion is between 1 and 3 millimeters.

30. The endodontic instrument of claim 26, wherein the length of the first portion is between 1 and 3 millimeters, the second cross-section approximates a rectangle, and every cross-section of the first portion approximates a square.

\* \* \* \* \*